United States Patent [19]

Young

[11] Patent Number: 5,156,600
[45] Date of Patent: Oct. 20, 1992

[54] BIDIRECTIONAL CHECK VALVE CATHETER

[75] Inventor: Thomas M. Young, Andover, Mass.

[73] Assignee: Strato Medical Corporation, Beverly, Mass.

[21] Appl. No.: 595,038

[22] Filed: Oct. 10, 1990

[51] Int. Cl.⁵ ............................................... A61M 5/00
[52] U.S. Cl. .................................... 604/247; 137/527
[58] Field of Search ...................... 604/247, 246, 248; 137/527, 527.8, 493, 493.8, 855

[56] References Cited

U.S. PATENT DOCUMENTS

| | | | |
|---|---|---|---|
| 386,461 | 7/1888 | Goll | 137/527 |
| 2,867,213 | 1/1959 | Thomas, Jr. | |
| 3,809,085 | 5/1974 | Bidwell | 604/247 |
| 4,180,068 | 12/1979 | Jacobsen et al. | |
| 4,301,833 | 11/1981 | Donald, III | 137/527 X |
| 4,431,426 | 2/1984 | Groshong et al. | 604/280 |
| 4,493,696 | 1/1985 | Uldall | 604/43 |
| 4,589,869 | 5/1986 | Wernborg | 604/247 |
| 4,657,536 | 4/1987 | Dorman | 604/247 |
| 4,671,796 | 6/1987 | Groshong et al. | 604/247 |
| 4,701,166 | 10/1987 | Groshong et al. | 604/247 |
| 4,705,501 | 11/1987 | Wigness et al. | 604/43 |

FOREIGN PATENT DOCUMENTS

| | | |
|---|---|---|
| 3512314 | 10/1986 | Fed. Rep. of Germany . |
| 2583386 | 12/1986 | France . |
| 1258396 | 12/1971 | United Kingdom . |
| 9009204 | 8/1990 | World Int. Prop. O. . |

*Primary Examiner*—John D. Yasko
*Attorney, Agent, or Firm*—Lahive & Cockfield

[57] ABSTRACT

A valved catheter is disclosed having an elongated, flexible tubular element extending along a central axis and a flow portion of a valve assembly which controls fluid flow in the tubular element. The element is adaptable for bidirectional flow of fluid between its proximal and its distal ends, with a bidirectional valve assembly coupled to the interior of the tubular element. The bidirectional assembly generally defines a control plane which intersects the central axis at an oblique angle. The assembly has an inflow portion and an outflow portion nominally disposed to lie in the control plane. The inflow portion includes an inflow vane positioned between the intersection of the control plane with the central axis and the distal end and which is adapted to be deflected out of the control plane toward the distal end in response to the establishment of a relatively high fluid pressure at the proximal end and a relatively lower fluid pressure at the distal end. The outflow portion also includes an outflow vane positioned between the intersection of the control plane with the central axis and the proximal end and which is adapted to be deflected out of the control plane toward the proximal end in response to the establishment of a relatively low fluid pressure at the proximal end and a relatively higher fluid pressure at the distal end.

43 Claims, 3 Drawing Sheets

BIDIRECTIONAL CHECK VALVE CATHETER

BACKGROUND OF THE INVENTION

The present invention relates to a catheter intended for implantation within a living body for long term usage, and more particularly to an implantable single lumen catheter having a bidirectional check valve for controlling fluid flow into and out of the catheter.

Various medical procedures require vascular access over a period of time. Such procedures may include implantation of a permanent intravascular device for portable drug infusion devices, for hemodialysis, or for cases where continuous blood work or access to the bloodstream is required. These procedures are often performed by using either transcutaneous or totally implanted catheters and fluid access devices.

There are problems associated with long term catheterization of a blood vessel. A first problem is infection at the skin puncture point, and a second problem is clotting of blood within the catheter lumen. The first problem may be solved by installing a subcutaneous fluid access assembly in a patient and which is coupled to the patient's bloodstream by means of an implanted catheter As for the second problem, in cases where the flow rate of the fluid carried by the catheter is very high, or perhaps if an anti-coagulant is carried by the fluid in the catheter, then the catheter will remain open to fluid flow over the long term. However, in situations with low fluid flow rates, or only intermittent fluid flow, clots or plugs may form inside of the catheter lumen, thus obstructing fluid flow. This limits the useful lifetime of the implanted catheter, or requires constant flushing or heparinization.

It has also been experienced that changes in blood pressure may cause a fluctuating pressure at the tip of an implanted catheter. Such fluctuation can induce a backflow of blood up the catheter. This blood is subject to clotting.

A known commercially available bidirectional check valve catheter features a slit valve. The tip of the catheter is closed and the side wall of the catheter near the tip is slit, to form the slit valve. The valve allows both aspiration of blood and infusion of fluids. The check valve precludes the diffusion of blood into the lumen when the catheter is not in use. This catheter is known as the Groshong catheter (available from Catheter Technology Corporation, Salt Lake City, Utah).

While various other valved catheters are also known, there is still a need for an improved implantable, bidirectional check valve catheter assembly with long useful life, which does not require special maintenance, and with low potential of formation of obstructions, such as emboli.

It is therefore an object of the present invention to provide an implantable catheter with a long useful life and which does not require special maintenance.

It is another object of the present invention to provide a check valve catheter which is resistant to occlusion from blood clot, and does not require heparinization.

It is yet another object of the present invention to provide an intravascular catheter with a bidirectional check valve which permits long term placement in the bloodstream without requiring flushing to keep the catheter lumen fluid flow path open.

SUMMARY OF THE INVENTION

The present invention provides an improved check valve catheter requiring low maintenance and having low likelihood of forming emboli or other obstructions.

In one aspect, the invention includes a valved catheter having an elongated, flexible tubular element extending along a central axis. In a preferred embodiment, the element is adapted for bidirectional flow of fluid between its proximal and its distal end, having a generally planar bidirectional valve assembly coupled to the interior of the tubular element. The assembly generally defines a control plane which intersects the central axis at an oblique angle. The assembly has an inflow portion and an outflow portion nominally (e.g., at rest) disposed to lie in the control plane. The inflow portion includes an inflow vane positioned between the intersection of the control plane with the central axis and the distal end and which is adapted to be deflected out of the control plane toward the distal end in response to the establishment of a relatively high fluid pressure at the proximal end and a relatively lower fluid pressure at the distal end. The outflow portion also includes an outflow vane positioned between the intersection of the central plane with the central axis and the proximal end and which is adapted to be deflected out of the control plane toward the proximal end in response to the establishment of a relatively low fluid pressure at the proximal end and a relatively higher fluid pressure at the distal end.

Embodiments of the invention may include several variations. The valve assembly may be other than generally planar, and the control plane may be a nominal control plane. The valve assembly may include resilient and deflectable portions such that the inflow vane is displaceable by flexing in a first direction generally along the central axis and the outflow vane is displaceable by flexing in a second direction opposite to the first direction generally along the central axis.

In one form, for an elliptical or circular cross-section catheter, the assembly includes a flexible elliptical disk-shaped element which nominally lies in the control plane. At least a part of the periphery of the elliptical disk-shaped element is affixed to the interior of the tubular element. The elliptical disk-shaped element defines two disk axes normal to the central axis. The two disk axes include a major axis and a minor axis which is normal to the major axis. The periphery of the elliptical disk-shaped element which is located about (such as at and adjacent to) the minor axis is affixed to the interior of the tubular element along a first portion and a second portion of the periphery. A third portion of the periphery defines the inflow vane and is located at and adjacent to the major axis, displaceable in a first direction generally along the central axis. A fourth portion of the periphery defines the outflow vane and is located at and adjacent to the major axis, displaceable in a second direction opposite to the first direction generally along the central axis. Either vane may be defined by an arcuate segment of the disk-shaped element located about the major axis.

The peripheral edges of the vanes cooperate with the nominally adjacent inner surfaces of the catheter to control the fluid flow therethrough. Preferably, the inflow vane is adapted to be displaced out of the control plane when a fluid pressure differential is developed in the tubular element based upon a higher pressure in the proximal end than in the distal end in excess of a first predetermined value. The outflow vane is adapted to be displaced out of the control plane when a fluid pressure differential is developed in the tubular element base upon a higher pressure in the distal end than in the proximal end in excess of a second predetermined value. The inflow vane is substantially resistant to flow of fluid from the distal end to the proximal end, and the outflow vane is substantially resistant to flow of fluid from the proximal end to the distal end.

In another aspect of the invention, the assembly may include a disk-shaped element which is affixed to the interior of the tubular element at all points along the periphery of the disk-shaped element. The inflow vane is defined by an arcuate slit in the inflow portion and the outflow vane is defined by an arcuate slit in the outflow portion.

Generally, the valve assembly is nominally disposed to prevent fluid flow in the tubular element where there is substantially no fluid pressure differential across the valve assembly.

BRIEF DESCRIPTION OF THE DRAWINGS

These and other advantages of the present invention will be more fully understood by reference to the following detailed description in conjunction with the attached drawing in which.

DETAILED DESCRIPTION OF THE PREFERRED EMBODIMENT

Figure 1:
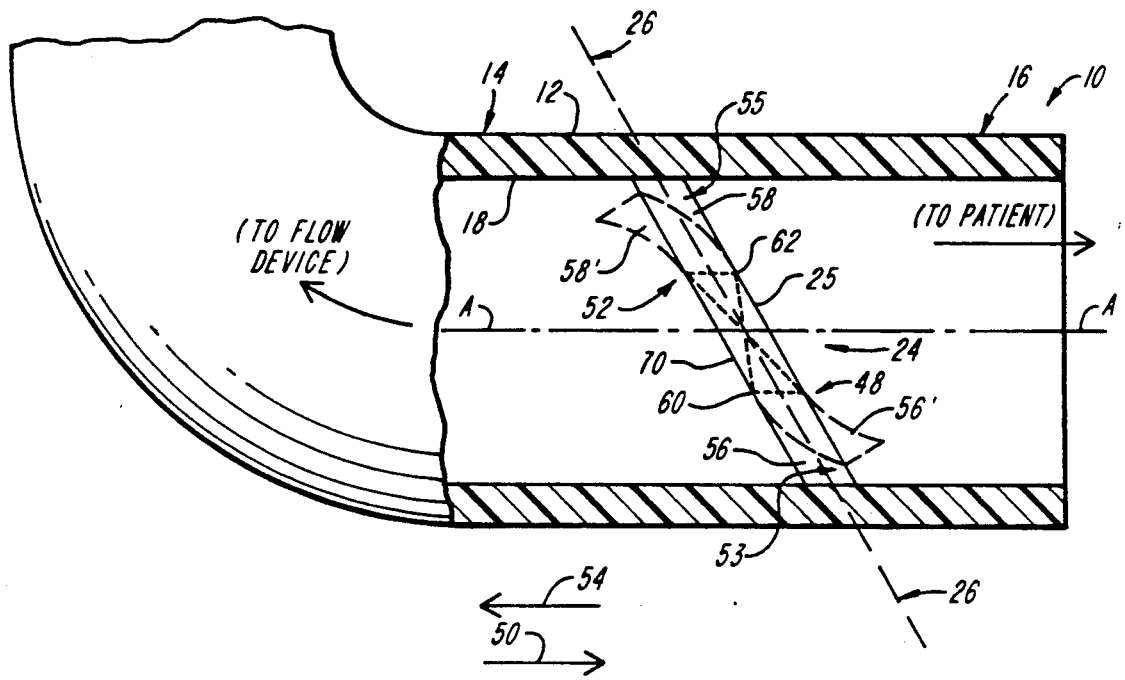
FIG. 1 is a side cross-section of a catheter segment incorporating the present invention.
Figure 2:
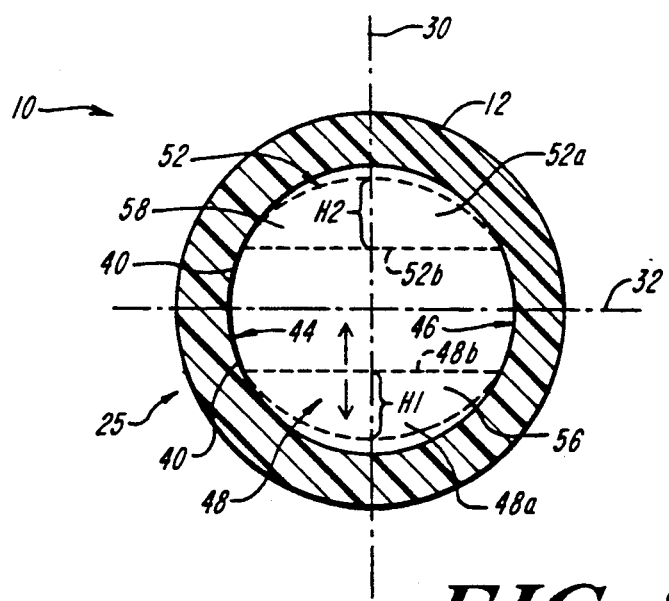
FIG. 2 is a cross-section of valve assembly 25 through plane 26 of FIG. 1.

An embodiment of the present invention is shown in FIGS. 1 and 2 where catheter check valve assembly 10 includes a flexible tubular element 12, such as a catheter. Catheter 12 has a first or proximal end 14 and a second or distal end 16, and is disposed, when implanted in a patient, for inflow of fluid from proximal end 14 to distal end 16 into the patient's bloodstream, and for outflow of fluid from the patient from distal end 16 to proximal end 14 to a connected flow device, such as a syringe. Catheter 12 further includes an interior cylindrical wall structure 18 which extends along a central axis A and thus defines a bidirectional fluid flow path. The catheter is preferably formed of biocompatible material such as silicone or polyurethane.

Coupled to catheter interior wall 18 is a nominally planar bidirectional valve assembly 24. For the circular cross-section catheter of FIGS. 1 and 2, the valve assembly 24 is generally defined as an elliptical disk-shaped element 25. With different catheter cross-sections, however, the disk-shaped element may have a correspondingly different shape.

The valve assembly nominally lies in a control plane 26 at an oblique angle to central axis A. Valve assembly 24 is generally resistant to fluid flow except as permitted by a valving arrangement such as described below. Valve assembly 24 is preferably formed of a resilient material, such as silicone or polyurethane.

The disk-shaped element 25 of assembly 24 extends along two disk axes normal to the catheter central axis A. These two disk axes include a major axis 30, and a minor axis 32, where these axes are normal to each other, substantially coinciding with the major and minor axes, respectively of the ellipse defined by element 25. A first disk peripheral portion 44 and a second peripheral portion 46 of the periphery 40 of disk-shaped element 25, as respectively located about the minor axis 32, are affixed to the interior 18 of the catheter. A third portion 48 of the disk periphery 40 defines an inflow vane 56, located about major axis 30, which is displaceable in a first direction 50 from the proximal end 14 to the distal end 16 generally along the central axis A. A fourth portion 52 of periphery 40 defines an outflow vane 58, located about major axis 30, which is displaceable in a second direction 54, opposite to the first direction 50, also generally along the central axis A.

Hence, inflow vane 56 is adapted to be displaced out of the control plane (as indicated by the deflected vane 56' shown in phantom in FIG. 1) to open a fluid flow path 53 when a fluid pressure differential is developed in the catheter with a sufficiently high pressure in the proximal end 14 and sufficiently low pressure in the distal end 16. As well, the outflow vane 58 is adapted to be displaced out of the control plane (as indicated by the deflected vane 58' shown in phantom in FIG. 1) to open a fluid flow path 55 when the fluid pressure differential is developed in the catheter with a sufficiently higher pressure in the distal end 16 than in the proximal end 14.

Inflow vane 56 is defined as an arcuate section 48a of the disk which pivots about a pivot axis 48b and outflow vane 58 is defined by an arcuate section 52a which pivots about pivot axis 52b. Location of axes 48b, 52b determines the height H1, H2 of vane 56. In the sense of the vanes being lever arms, heights H1, H2 determine the amount of deflection (deflectability) of the respective vane for a given fluid pressure and flexibility of the material of valve assembly 24.

As well, scorings 60, 62 on disk 25 opposite to the side of the disk on which the vane 56 or 58 deflects and along a respective deflection axis 48b, 52b, also may be employed to establish flexure regions which regulate the deflectability of the respective vanes 56, 58. Furthermore, it is possible to select different depths of scorings 60, 62 and different vane heights, H1, H2, such that vanes 56, 58 will deflect differently according to their resulting respective deflectabilities. Consequently, a bidirectional valve may be obtained having a high pressure direction and a low pressure direction. The advantage of this two level effect is that infusion therapy may be tailored for use with special apparatus such as pumping devices. As well, valves may be optimized for varying pressures at the point of implant or for use with fluids of different viscosities (i.e.: blood or water) or for use with a variety of infusion devices (i.e.: pumps or bags).

Preferably, the inflow vane is substantially resistant to outflow of fluid from the distal end toward the proximal end 14, and the outflow vane is substantially resistant to outflow of fluid from the proximal end 14 to the distal end 16.

Figure 3:
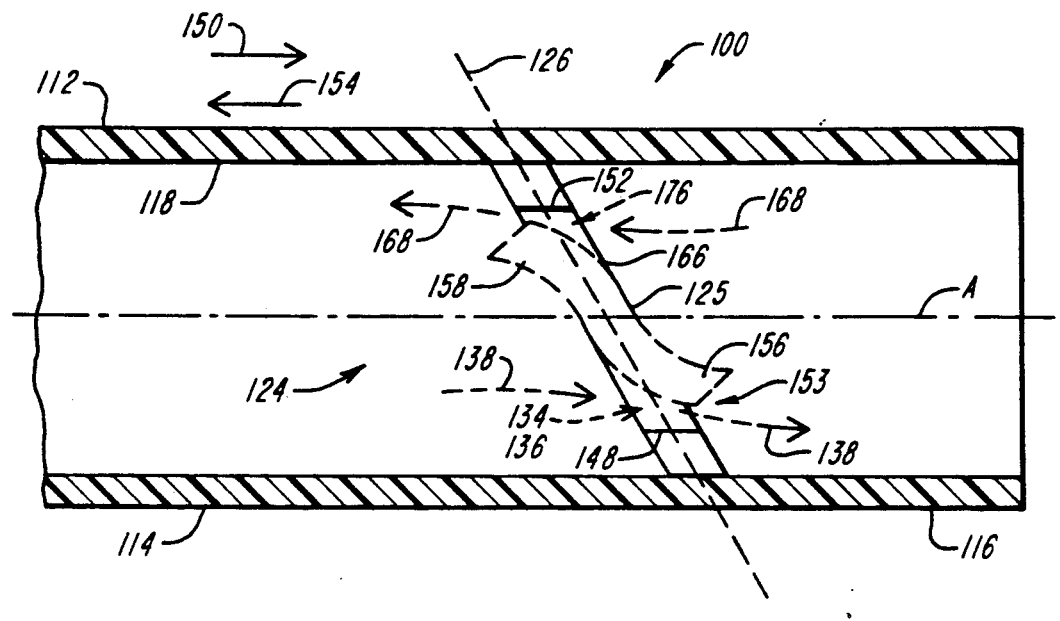
FIG. 3 is a side-cross section of a catheter segment incorporating an alternative embodiment of the present invention.
Figure 4:
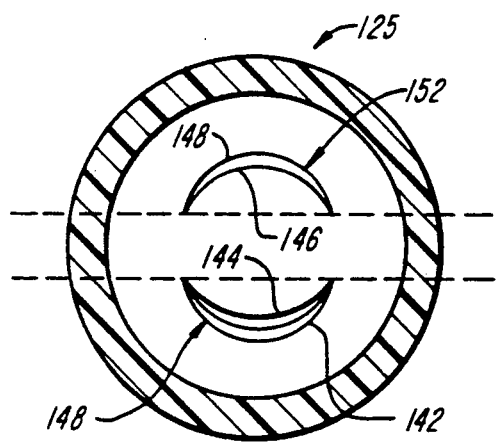
FIG. 4 is a cross-section of valve assembly 125 through plane 126 of FIG. 3.

In an alternative embodiment of the invention, as shown in FIGS. 3 and 4, a valve assembly 124 of catheter check valve assembly 100 includes an elliptical disk-shaped element 125 which lies in control plane 126 at an oblique angle to catheter central axis A. The entire periphery of disk 125 is affixed at respective locations along the interior wall 118 of catheter 112. Hence this valve assembly 124 is generally resistant to fluid flow in the catheter except as permitted by vanes 156, 158 as described below. The catheter has a proximal end 114 and a distal end 116. The catheter is shown in FIG. 4 as circular in cross-section, but elliptical or other cross-sections are also within the scope of the present invention.

In this embodiment, Slit 148 piercing entirely through a section of disk 125, creates a flexible flap or vane 156. Slit 152, piercing entirely through another section of disk 125, creates a flexible flap or vane 158. Vanes 156, 158 are adapted to be deflected out of the control plane 126, but in opposite directions, generally along central axis A.

Slit 148 is defined by two edges 142, 144 formed in valve member 125, and slit 152 is formed by edges 146, 148 also formed in valve member 125. These edges are nominally substantially parallel to the central axis A. In FIG. 4, both vanes 142 and 152 are shown in an open position. This is for ease of description only, since it will be appreciated that the valve assembly is generally intended to operate with one valve or both valves closed, but not with both valves open.

Slit 148 and vane 156 are configured such that inflow of fluid 151 along direction 150 (see arrow 150) impinging against inner wall 134 of vane 156 will deflect vane 156 (as shown in dotted outline) along the direction 150 away from control plane 126, and thereby opening a fluid flow path (see dotted arrow 136) for the flow of fluid (see dotted arrows 138) in the direction 150 from proximal end 114 to distal end 116. The amount of deflection of vane 156 is a function of the fluid pressure differential on the proximal and distal sides of disk 125 and the deflectability of the vane.

Vane 158 is similarly configured such that outflow of fluid (see dotted arrows 168) along direction 154 (see arrow 154) is caused by fluid pressure mounting up on the outer wall 166 of vane 158 and deflecting vane 158 toward proximal end 114 (as shown in dotted outline) in the direction 154, opening a fluid flow path 176 for flow of fluid (see dotted arrows 168) also as a function of the fluid pressure differential and vane deflectability.

In this embodiment, vane deflectability may be controlled by controlling the arc length of slits 148, 152, and also by scoring the disk as in the manner earlier described with respect to the embodiment of FIGS. 1 and 2. Deflectability may also be regulated by varying the thickness of the disk, i.e., having a thicker (harder to deflect) inflow vane than the outflow vane, for example.

It will now be appreciated that in view of the simplicity of the present invention, a respective valve assembly may be employed in each lumen of a multi-lumen catheter, so as to afford independent bi-directional control to each of the lumen, and in which case FIGS. 1-2 and 3-4 will be understood to show one lumen of a respective multiple lumen catheter.

While a generally planar valve assembly has been described, an S-shaped or other non-planar or non-symmetrical valve assembly may also be employed within the invention, and therefore discussion of a control plane may be understood as generally encompassing a control plane or a nominal control plane.

In two further preferred embodiments, as shown in FIGS. 5 A,B, the valve assembly takes the form of an elongate flexible element 224 or 324, nominally mounted relative to a respective control plane 226, 326 to form vanes 256, 258 and vanes 356, 358, respectively.

Vanes 256, 258 and vanes 356, 358 function generally as do vanes 56, 58 of FIGS. 1 and 2.

Figure 5A:
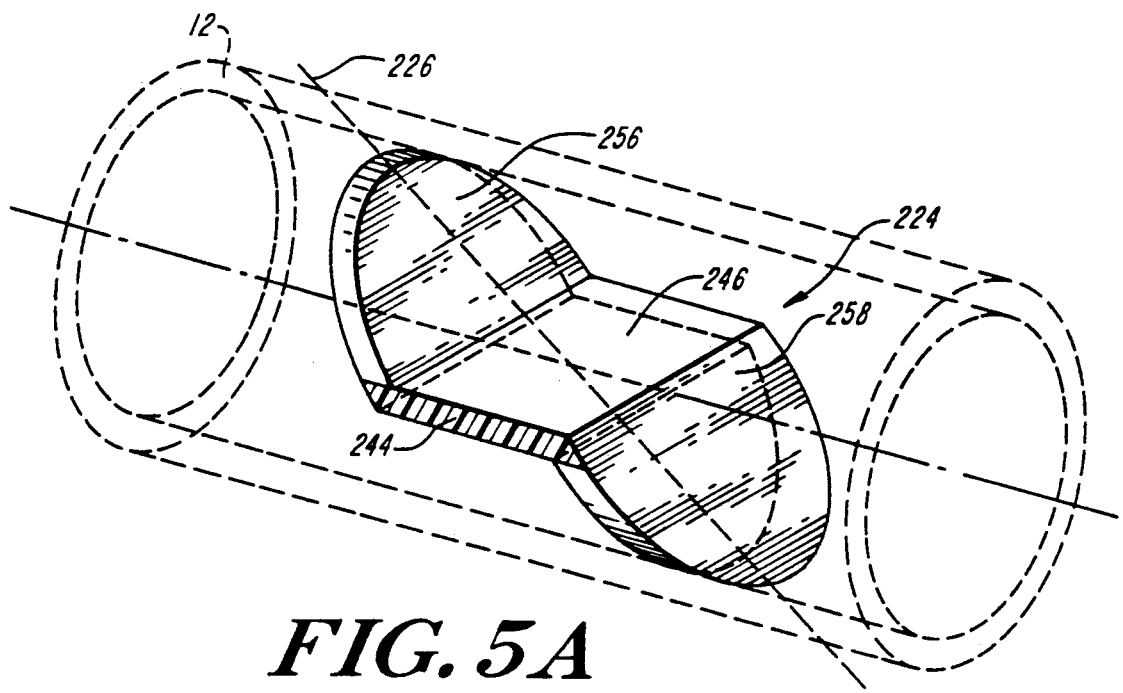
FIGS. 5A,B are perspective views of additional preferred embodiments of a valve assembly of the present invention.

More particularly, as shown in FIG. 5A, element 224 is affixed to the interior of catheter 12 only at its edge portions 244, 246 to create vanes 256, 258. Vanes 256, 258 form mechanical closures against the catheter interior.

Figure 5B:
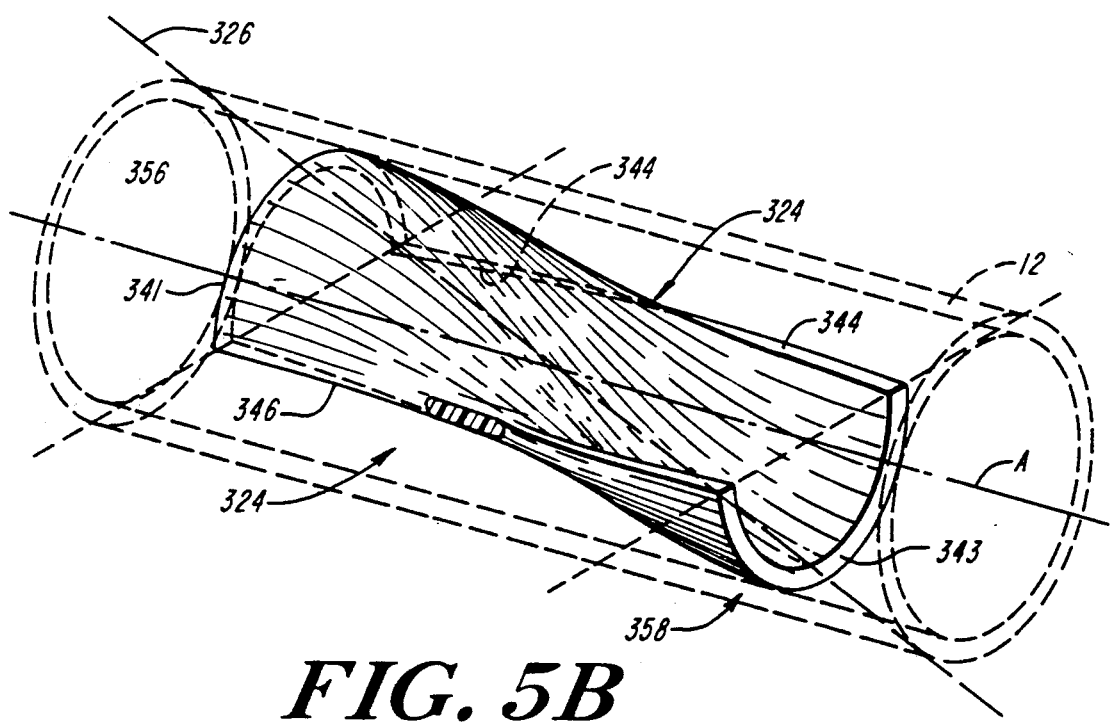

In FIG. 5B, element 324 is a contoured structure preferrably molded from a flexible material (such as LIM-type silicone rubber), and is affixed to the interior of catheter 12 along a first pair of the element's sides 344, 346. The opposed ends 341, 343 of element 324 are mechanically urged against the interior of the catheter to create vanes 356, 358. Flexible element 324 is preferrably formed thinner than the wall thickness of the catheter in which it is to be used. Hence, an element having a thickness of about 0.010–0.020 inches can be beneficially mated with a catheter having a wall thickness of about 0.020–0.025 inches, for example.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed:

1. A valved catheter comprising
   (a) an elongated, flexible tubular element extending along a central axis and having a proximal end and a distal end, and adapted for flow of fluid between said proximal and said distal end, and
   (b) a valve assembly coupled to the interior of the tubular element, said assembly generally defining a nominal control plane which intersects said central axis at an oblique angle, said assembly having a flow portion nominally disposed to lie in said control plane whereby said assembly establishes a fluid seal across the interior of said tubular element at said control plane, said flow portion including a flexible vane having its periphery affixed at least in part to the interior of said tubular element and positioned between said intersection of said control plane with said central axis and said distal end and adapted to be deflected out of said control plane toward said distal end only in response to the establishment of a relatively high fluid pressure at said proximal end and a relatively low fluid pressure at said distal end.

2. The catheter of claim 1 wherein said element is adapted for bidirectional flow of fluid and wherein said valve assembly is a bidirectional valve assembly, said flow portion having an inflow portion and an outflow portion nominally disposed to lie in said control plane wherein said assembly establishes a fluid seal across the interior of said tubular element at said control plane, said inflow portion including a flexible inflow van positioned between said intersection of said control plane with said central axis and said distal end and adapted to be deflected out of said control plane toward said distal end only in response to the establishment of a relatively high fluid pressure at said proximal end and a relatively low fluid pressure at said distal end, and said outflow portion including a flexible outflow vane positioned between said intersection of said central plane with said central axis and said proximal end and adapted to be deflected out of said control plane toward said proximal end only in response to the establishment of a relatively low fluid pressure at said proximal end and a relatively high fluid pressure at said distal end.

3. The catheter of claim 2 wherein said bidirectional valve assembly comprises resilient and deflectable portions such that said inflow vane is displaceable by flexing in a first direction generally along said central axis and said outflow vane is displaceable by flexing in a second direction opposite to said first direction generally along said central axis.

4. The catheter of claim 2 wherein said tubular element defines a substantially circular cross-section interior region extending along said central axis and said assembly includes a flexible elliptical disk-shaped element which nominally lies in said control plane.

5. The catheter of claim 4 wherein at least a part of the periphery of said elliptical disk-shaped element is affixed to the interior surface of said tubular element.

6. The catheter of claim 5 wherein said elliptical disk-shaped element defines two disk axes normal to said central axis, said two disk axes including a major axis and a minor axis which is normal to said major axis, the periphery of said elliptical disk-shaped element located about said minor axis being affixed to the interior of said tubular element along a first portion and a second portion of said periphery, a third portion of said periphery defining said inflow vane located about said major axis and being displaceable in a first direction generally along said central axis, and a fourth portion of said periphery defining said outflow vane located about said major axis and being displaceable in a second direction opposite to said first direction generally along said central axis.

7. The catheter of claim 6 wherein said inflow vane is defined by an arcuate segment of said disk-shaped element located about said major axis.

8. The catheter of claim 6 wherein said outflow vane is defined by an arcuate segment of said disk-shaped element located about said major axis.

9. The catheter of claim 6 wherein said periphery first portion and said periphery second portion are generally positioned in opposition to each other.

10. The catheter of claim 6 wherein said periphery third portion and said periphery fourth portion are generally positioned in opposition to each other.

11. The catheter of claim 2 wherein said valve assembly is entirely internal to said tubular element.

12. The catheter of claim 2 wherein said valve assembly is affixed to the interior of said tubular element at all points along the periphery of said disk-shaped element.

13. The catheter of claim 12 wherein said inflow vane is defined by an arcuate slit in said inflow portion and said outflow vane is defined by an arcuate slit in said outflow portion.

14. The catheter of claim 2 wherein the valve assembly includes a disk-shaped element nominally disposed to prevent fluid flow in said tubular element where there is substantially no fluid pressure differential across said valve assembly.

15. The catheter of claim 14 wherein the inflow vane is displaceable out of said control plane when a fluid pressure differential is developed in said tubular element based upon a higher pressure in said proximal end than in said distal end in excess of a first predetermined value.

16. The catheter of claim 14 wherein the outflow vane is displaceable out of said control plane when a fluid pressure differential is developed in said tubular element based upon a higher pressure in said distal end than in said proximal end in excess of a second predetermined value.

17. The catheter of claim 2 wherein said inflow vane is substantially resistant to flow of fluid from said distal end to said proximal end.

18. The catheter of claim 2 wherein said outflow vane is substantially resistant to flow of fluid from said proximal end to said distal end.

19. The catheter of claim 2 wherein said catheter includes multiple lumens, at least one of said multiple lumen comprising said tubular element.

20. The catheter of claim 2 wherein said bidirectional valve assembly is generally planar.

21. The catheter of claim 1 wherein said tubular element defines a substantially circular cross-section interior region extending along said central axis and said assembly includes a flexible elliptical disk-shaped element which nominally lies in said control plane.

22. The catheter of claim 21 wherein at least a part of the periphery of said elliptical disk-shaped element is affixed to the interior surface of said tubular element.

23. The catheter of claim 22 wherein said elliptical disk-shaped element defines two disk axes normal to said central axis, said two disk axes including a major axis and a minor axis which is normal to said major axis, the periphery of said elliptical disk-shaped element located about said minor axis being affixed to the interior of said tubular element along a first portion and a second portion of said periphery, a third portion of said periphery defining said flexible vane located about said major axis and being displaceable in a first direction generally along said central axis.

24. The catheter of claim 23 wherein said flexible vane is defined by an accurate segment of said disk-shaped element located about said major axis.

25. The catheter of claim 23 wherein said periphery first portion and said periphery second portion are generally positioned in opposition to each other.

26. The catheter of claim 1 wherein said valve assembly is entirely internal to said tubular element.

27. The catheter of claim 1 wherein said valve assembly is affixed to the interior of said tubular element at all points along the periphery of said disk-shaped element.

28. The catheter of claim 27 wherein said flexible vane is defined by an arcuate slit in said flow portion.

29. The catheter of claim 1 wherein the valve assembly includes a disk-shaped element nominally disposed to prevent fluid flow in said tubular element when there is substantially no fluid pressure differential across said valve assembly.

30. The catheter of claim 1 wherein said catheter includes multiple lumens, at least one of said multiple lumens comprising said tubular element.

31. The catheter of claim 1 wherein said valve assembly is generally planar.

32. A valved catheter comprising
 (a) an elongated, flexible tubular element extending along a central axis and having a proximal end and a distal end, and adapted for flow of fluid between said proximal and said distal end, and
 (b) a valve assembly coupled to the interior of the tubular element, said assembly generally defining a nominal control plane which intersects said central axis at an oblique angle, said assembly having a flow portion nominally disposed to lie in said control plane whereby said assembly establishes a fluid seal across the interior of said tubular element at said control plane, said flow portion including a flexible vane having its periphery affixed at least in part to the interior of said tubular element and positioned between said intersection of said control plane with said central axis and said proximal end and adapted to be deflected out of said control plane toward said proximal end only in response to the establishment of a relatively high fluid pressure at said distal end and a relatively low fluid pressure at said proximal end.

33. The catheter of claim 32 wherein said tubular element defines a substantially circular cross-section interior region extending along said central axis and said assembly includes a flexible elliptical disk-shaped element which nominally lies in said control plane.

34. The catheter of claim 33 wherein at least a part of the periphery of said elliptical disk-shaped element is affixed to the interior surface of said tubular element.

35. The catheter of claim 34 wherein said elliptical disk-shaped element defines two disk axes normal to said central axis, said two disk axes including a major axis and a minor axis which is normal to said major axis, the periphery of said elliptical disk-shaped element located about said minor axis being affixed to the interior of said tubular element along a first portion and a second portion of said periphery, a third portion of said periphery defining said flexible vane located about said major axis and being displaceable in a first direction generally along said central axis.

36. The catheter of claim 35 wherein said flexible vane is defined by an arcuate segment of said disk-shaped element located about said major axis.

37. The catheter of claim 35 wherein said periphery first portion and said periphery second portion are generally positioned in opposition to each other.

38. The catheter of claim 32 wherein said valve assembly is entirely internal to said tubular element.

39. The catheter of claim 32 wherein said valve assembly is affixed to the interior of said tubular element at all points along the periphery of said disk-shaped element.

40. The catheter of claim 39 wherein said flexible vane is defined by an arcuate slit in said flow portion.

41. The catheter of claim 32 wherein the valve assembly includes a disk-shaped element nominally disposed to prevent fluid flow in said tubular element when there is substantially no fluid pressure differential across said valve assembly.

42. The catheter of claim 32 wherein said catheter includes multiple lumens, at least one of said multiple lumens comprising said tubular element.

43. The catheter of claim 32 wherein said valve assembly is generally planar.

* * * * *